United States Patent [19]

Murray

[11] Patent Number: 5,660,445
[45] Date of Patent: Aug. 26, 1997

[54] SUPINE POSITION RESTRAINT HARNESS

[75] Inventor: Connie Murray, Tequesta, Fla.

[73] Assignee: E-Z-ON Products, Inc., Jupiter, Fla.

[21] Appl. No.: 616,196

[22] Filed: Mar. 14, 1996

[51] Int. Cl.⁶ .................................................. A47C 31/00
[52] U.S. Cl. ........................ 297/485; 297/466; 297/484; 297/DIG. 6
[58] Field of Search ................................ 297/464, 466, 297/468, 485, DIG. 6, 484; 280/801.1

[56] References Cited

U.S. PATENT DOCUMENTS

| | | | |
|---|---|---|---|
| 2,833,344 | 5/1958 | Lucht | 155/189 |
| 2,979,028 | 4/1961 | Zakely | 119/96 |
| 3,099,486 | 7/1963 | Scott | 297/389 |
| 3,428,029 | 2/1969 | Klickstein et al. | 119/96 |
| 4,004,583 | 1/1977 | Johnson | 297/466 X |
| 4,143,914 | 3/1979 | Klich | 297/389 |
| 4,226,474 | 10/1980 | Rupert et al. | 297/484 |
| 4,632,425 | 12/1986 | Barratt | 280/801 |
| 5,076,598 | 12/1991 | Nauman | 230/202 |
| 5,080,191 | 1/1992 | Sanchez | 182/3 |
| 5,131,682 | 7/1992 | Reed | 297/468 X |
| 5,226,698 | 7/1993 | Harrison | 297/485 |
| 5,435,272 | 7/1995 | Epstein | 119/770 |

*Primary Examiner*—Milton Nelson, Jr.
*Attorney, Agent, or Firm*—Pennie & Edmonds LLP

[57] ABSTRACT

A restraint harness is disclosed for securing a passenger to a seat in a vehicle. The harness is particularly well adapted for transporting a passenger who is in a supine or prone position. The harness has a pair of lateral torso straps adapted to be placed around the torso of the passenger and fastened together. A pair of shoulder straps extend over the shoulders and intersect with the torso straps. A pair of thigh straps extend from one of the torso straps and encompass the passengers thighs. A leg strap encompass the passenger's legs. Existing vehicle seat belts fasten to the torso straps and the to the leg strap to secure the passenger to the seat.

17 Claims, 6 Drawing Sheets

SUPINE POSITION RESTRAINT HARNESS

TECHNICAL FIELD OF THE INVENTION

The present invention relates to a restraining harness for securing a passenger to a vehicle seat, and more particularly, to a restraining harness for securing a passenger to a vehicle seat, wherein the passenger is in a supine or prone position.

BACKGROUND OF THE INVENTION

Seat belts are commonly used in passenger vehicles to secure a passenger to a seat, the seat belt typically fastens around the waist of the passenger. In the event of an accident, the seat belt restrains the passenger to the seat instead of the passenger experiencing free flight in the cab of the vehicle. Seat belts in modern vehicles include a shoulder strap and a waist strap to better restrain the passenger's torso against the seat and the seat back in the event of an accident.

Restraint harnesses have been commonly used in vehicles to secure children passengers to bench seat. For example, U.S. Pat. No. 4,226,474 issued to Rupert et al. discloses a restraint vest that utilizes a pair of straps that laterally encircle the torso of the wearer with a pair of straps that extend from the anterior side of the torso over the shoulders to the posterior side of the torso. Anchoring straps are secured to the seat back or to the floor to secure the vest to the seat.

Nevertheless, the restraint harnesses available today are useless when a passenger is wearing an appliance, such as a leg cast, body cast, brace, or any other appliance that affects the lower limbs, because the appliance often requires that the passenger be transported in a supine position with the torso of the passenger and the appliance being secured to the seat.

Therefore, what is needed is a restraint harness that is designed for securing a passenger who is wearing a lower limb appliance to a seat while the passenger is in a supine position.

DISCLOSURE OF THE INVENTION

It is, therefore, an object of the present invention to provide a restraint harness for securing a passenger to a vehicle seat, while the passenger is in a supine or prone position.

It is also an object of the present invention to provide a restraint harness for securing a passenger to a vehicle seat, wherein the passenger is wearing an appliance on a lower limb, such as a leg cast, a body cast, or a brace.

It is also an object of the present invention to provide a restraint harness for securing a passenger and the passenger's lower limbs to a vehicle seat in a supine position, even if a portion of one of the lower limbs is encased in a cast or a brace.

It is also an object of the present invention to provide a restraint harness for securing a passenger to a vehicle seat, wherein the restraint harness is adjustable in diameter and in length to accommodate different passenger torso sizes.

It is also an object of the present invention to provide a restraint harness for securing a passenger to a vehicle seat, wherein the harness may be utilized with existing vehicle seat belts.

It is also an object of the present invention to provide a restraint harness that is easily applied to and removed from the passenger, and wherein the harness is lightweight and easily portable.

According to the present invention, a restraint harness has a plurality of straps for securing a passenger in a supine or prone position to an existing seat, wherein existing seat belts fasten to the harness to secure the passenger to the seat. A pair of torso straps laterally encircle or encompass the torso of the wearer, the first torso strap is positioned approximately around the hip of the wearer and the second torso strap is positioned approximately around the chest of the wearer. A pair of shoulder straps extend anteriorly and posteriorly from the shoulders and intersect with and are secured to each of the torso straps at the intersection points. A pair of thigh straps extend from the torso strap at the hips to encircle and fasten around each of the wearer's thighs.

The torso straps have an adjustable fastening means so that the harness may be placed on the wearer, fastened together, and adjusted for proper fit. The shoulder straps also each have an adjustable fastening means, therefore the restraint harness is adjustable in width and in length to fit a wide variety of torso sizes. An adjustable leg strap with fastening means encircles the wearer's legs. Existing seat belts fasten to the torso straps and to the leg strap to secure the supine passenger to the vehicle seat.

The foregoing and other advantages of the present invention will become more apparent from the following description and accompanying drawings.

BEST MODE FOR CARRYING OUT THE INVENTION

Figure 1:
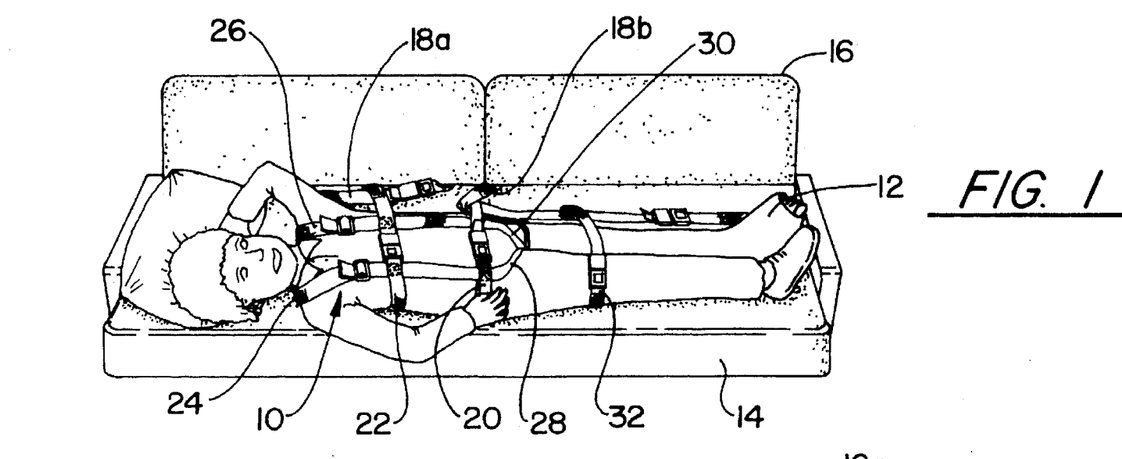
FIG. 1 is a front perspective view of a restraint harness of the present invention shown in use with an existing bench seat with seat belts.
Figure 2:
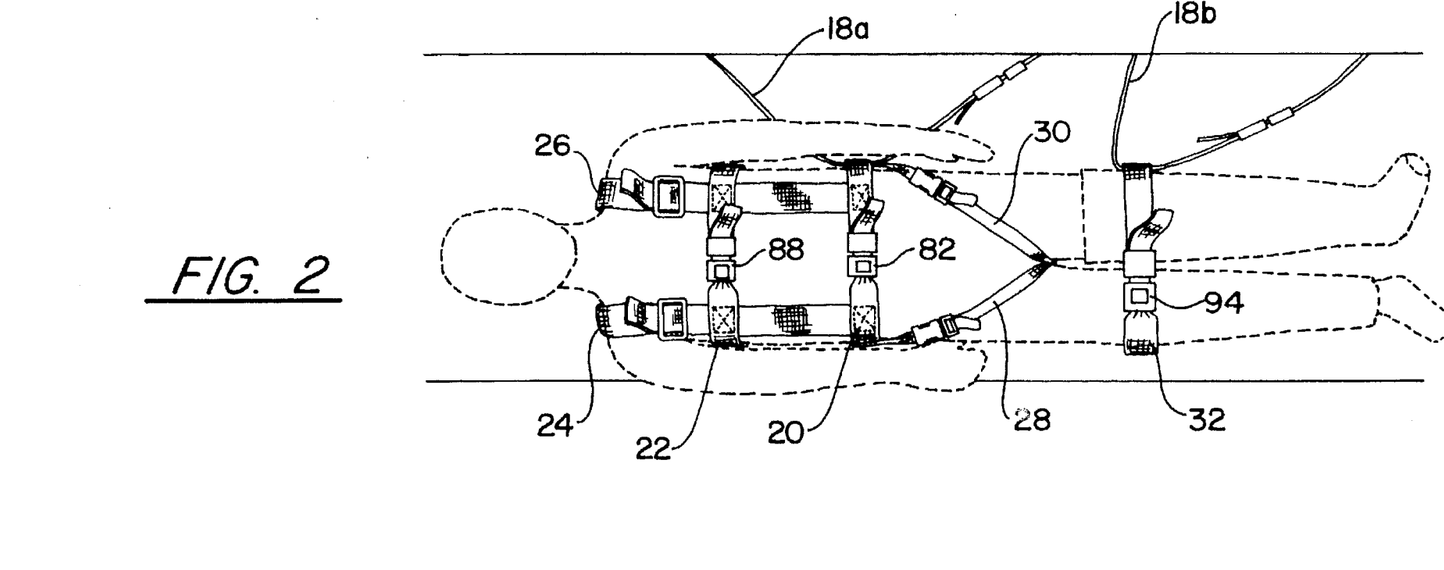
FIG. 2 is a top view of the restraint harness of the present invention shown in use with the existing bench seat with seat belts.

According to the present invention, and as shown in FIG. 1, a restraint harness 10 is disclosed that is used for securing a passenger to a bench type seat 14 in a vehicle, wherein the passenger is secured to the seat 14 while in a supine or prone position. The harness 10 is designed for use when a passenger has a physical condition which requires the wearing of a leg cast 12, leg brace, body cast, or any other appliance that would not allow for the passenger to be transported in the regular seated position or when the passenger is better suited for being transported in the supine position. The harness 10 of the present invention provides a means for securing the supine positioned passenger to the vehicle seat.

As shown in FIG. 1, the vehicle seat 14 has a seat back 16 that extends vertically upward from the horizontally positioned seat 14. The seat 14 has a first lap or shoulder belt 18a with a second lap or shoulder belt 18b juxtaposed to the first belt 18a. The belts 18 are secured to the seat 14 at the intersection of the seat 14 and the seat back 16.

FIG. 1 shows a passenger in a supine position on the seat 14. The passenger is secured to the seat 14 by the restraint harness 10 and the seat belts 18. The harness 10 has an anterior side 15, an opposite posterior side 17, a top or torso portion 11, and a bottom or lower limb portion 13. The torso portion 11 comprises a vest that has a plurality of torso straps. The lower limb portion 13 comprises a leg strap 32. The torso portion 11 more particularly comprises a hip or pelvic region strap 20, which generally laterally encircles or encompasses the hips of the wearer. The hip strap 20 is adapted to be positioned around the hips so as not to apply excess pressure to the soft tissue of the wearer. A chest strap 22 is generally parallel to the hip strap 20 and generally laterally encircles or encompasses the chest area of the wearer at about the apex of the rib cage. The chest strap 22 is adapted to be positioned at the apex of the rib cage so as not apply excess pressure to the soft tissue of the wearer, such at the underarm area.

A pair of shoulder straps are adapted to fit over the passenger's shoulders and to intersect with and be fastened to the hip strap 20 and the chest strap 22 at the intersection points. A right shoulder strap 24 extends from the right shoulder along the anterior side 15 to intersect with the chest strap 22 and the hip strap 20 at the anterior side 15. The right shoulder strap 24 also extends from the right shoulder along the posterior side 17 to intersect with the chest strap 22 and the hip strap 20 at the posterior side 17.

Likewise, a left shoulder strap 26, which is opposite to the right shoulder strap 24, extends from the left shoulder along the anterior side 15 to intersect with the chest strap 22 and then the hip strap 20 on the anterior side 15. The left shoulder strap 26 also extends from the left shoulder along the posterior side 17 to intersect with the chest strap 22 and the hip strap 20. The left and the right shoulder straps 24 and 26 are generally parallel with each other.

A right thigh strap 28 extends from a center point 52 at the posterior side of the hip strap to the anterior side of the hip strap. The right thigh strap 28 is adapted to be placed around the right inner thigh of the passenger from the posterior side and then be connected to the hip strap 20 at the anterior side. Likewise, a left thigh strap 30 extends from the center point 52 at the posterior side of the hip strap to the anterior side of the hip strap. The left thigh strap 30 is adapted to be placed around the left inner thigh of the passenger from the posterior side and then be connected to the hip strap 20 at the anterior side. The thigh straps 28 and 30 are intended to prevent the harness 10 from shifting longitudinally, or riding up on, the passenger.

The leg strap 32 is adapted to be wrapped around the passenger's legs, including any appliance, such as a cast 12 as shown in FIG. 1. The leg strap 32, when assembled on the passenger, is generally parallel to the hip strap 20 and to the chest strap 22. The leg strap 32 stabilizes the injured leg by securing the injured leg and the lower limb appliance to the passenger's other leg.

Figure 3:
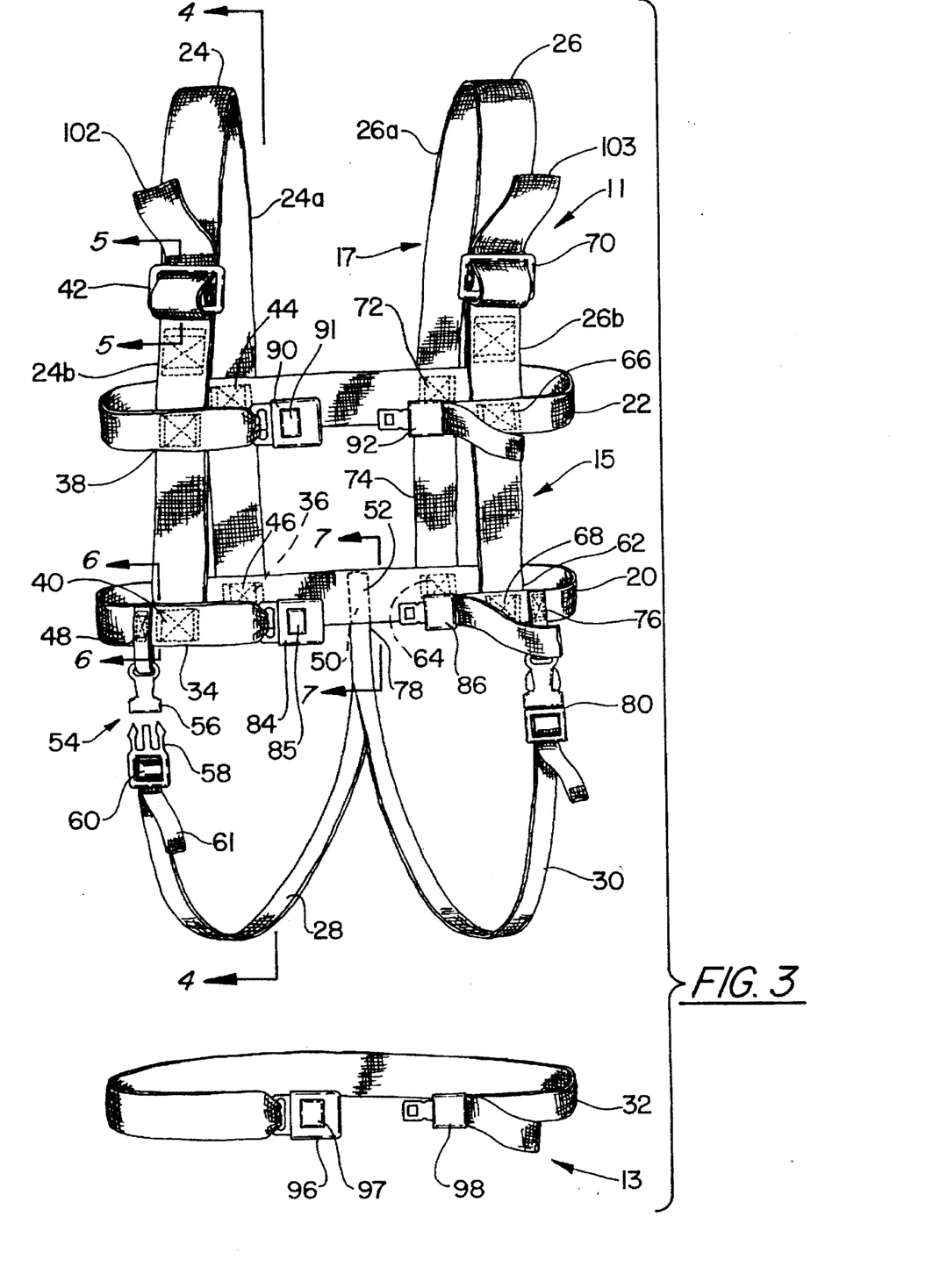
FIG. 3 is a front perspective view of the restraint harness of the present invention.

As shown in FIG. 3, the right shoulder strap 24 has a first end 34 adjacent to the hip strap 20 at the anterior side 15 and a second end 36 adjacent to the hip strap 20 at the posterior side 17. The right shoulder strap 24 intersects at the anterior side 15 with the chest strap 22 at intersection point 38 and with the hip strap 20 at intersection point 40, which is adjacent to the right shoulder strap first end 34. The right shoulder strap 24 intersects at the posterior side 17 with the chest strap 22 at intersection point 44 and with the hip strap 20 at intersection point 46, which is adjacent to the right shoulder strap second end 36. The straps are sewn together at the intersection points using nylon stitching.

Likewise, the left shoulder strap 26 has a first end 62 adjacent to the hip strap 20 at the anterior side 15 and a second end 64 adjacent to the hip strap 20 at the posterior side 17. The left shoulder strap 26 intersects at the anterior side 15 with the chest strap 22 at intersection point 66 and with the hip strap 20 at intersection point 68, which is adjacent to the right shoulder strap first end 62. The left shoulder strap 26 intersects at the posterior side 17 with the chest strap 22 at intersection point 72 and with the hip strap 20 at intersection point 74, which is adjacent to the left shoulder strap second end 64. The straps are sewn together at the intersection points using nylon stitching.

Figure 4:
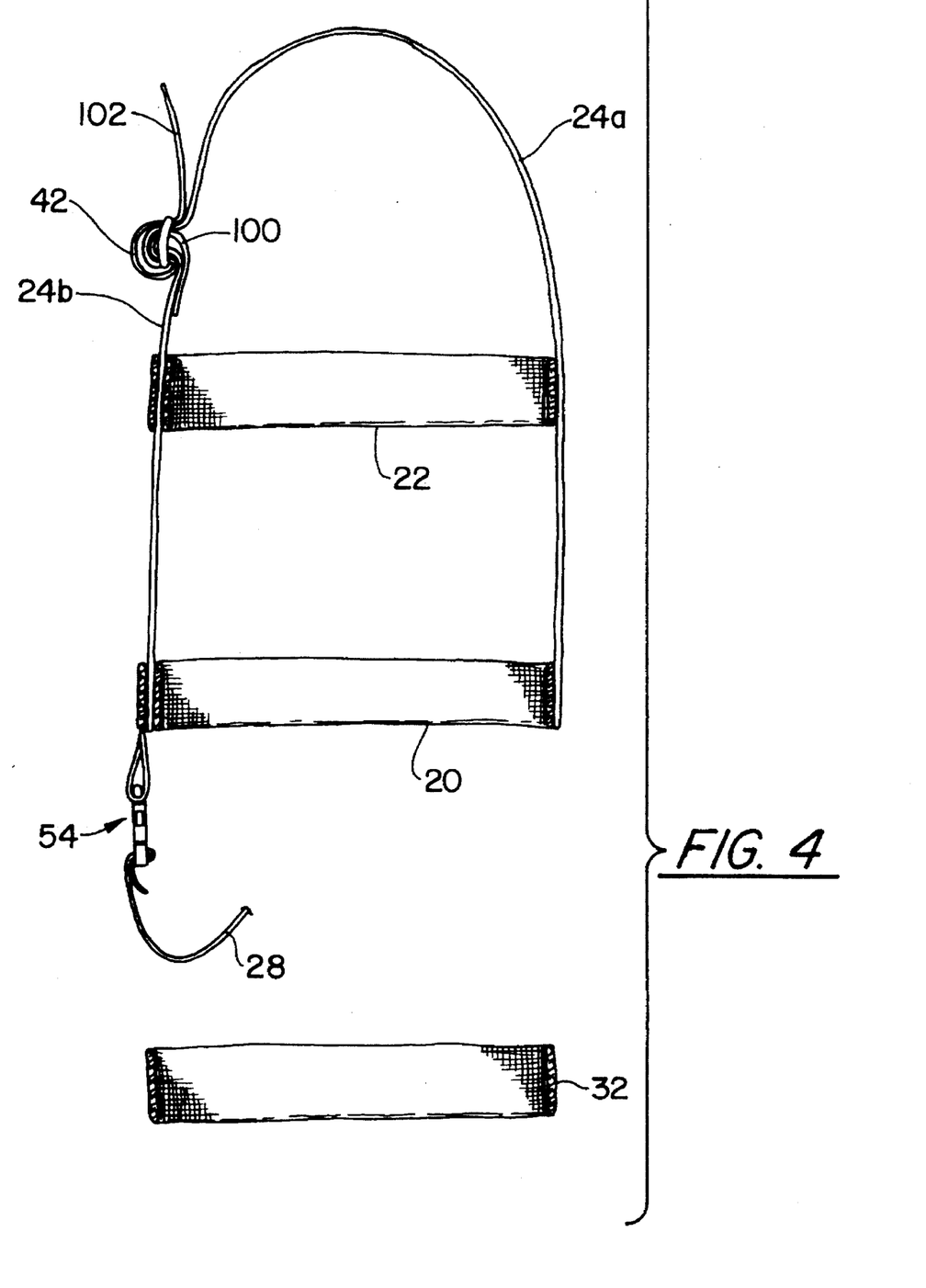
FIG. 4 is a partial cross sectional view of the restraint harness of the present invention taken from line 4—4 of FIG 3.
Figure 5:
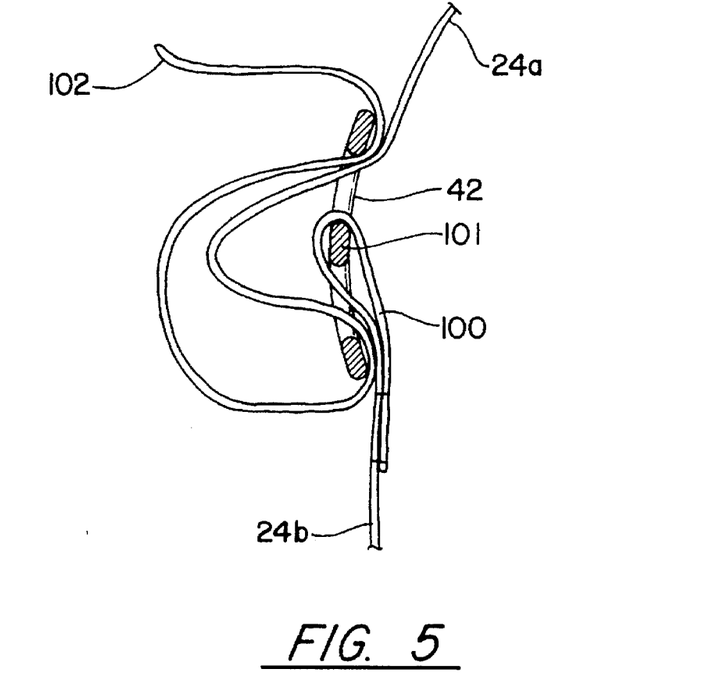
FIG. 5 is a partial cross sectional view taken from line 5—5 of FIG. 3, showing a right shoulder strap adjustment of the present invention.

As shown in FIG. 4 the right shoulder strap 24 comprises a posterior portion 24a and an opposite anterior portion 24b. Likewise, the opposite left shoulder strap 26 comprises a posterior portion 26a and an opposite anterior portion 26b. The right shoulder strap 24 anterior and posterior portions cooperate with each other by a length adjustable slide fastener 42 as shown in FIG. 5. The fastener 42 is a simple buckle wherein the right shoulder strap portion 24b has a loop 100 secured to a post 101 and the right shoulder strap portion 24a and strap extension 102 is fed through the adjuster 42 so as to allow the length of the right shoulder strap 24 to be adjusted to a variety of lengths.

Likewise, the left shoulder strap 26 has a length adjustable slide fastener 70, which is a simple buckle wherein the left shoulder strap portion 26b has a loop secured to a post and left shoulder strap portion 26a and left strap extension 103 is fed through the adjuster 70 so as to allow the length of the left shoulder strap 26 to be adjusted to a variety of lengths.

Figure 6:
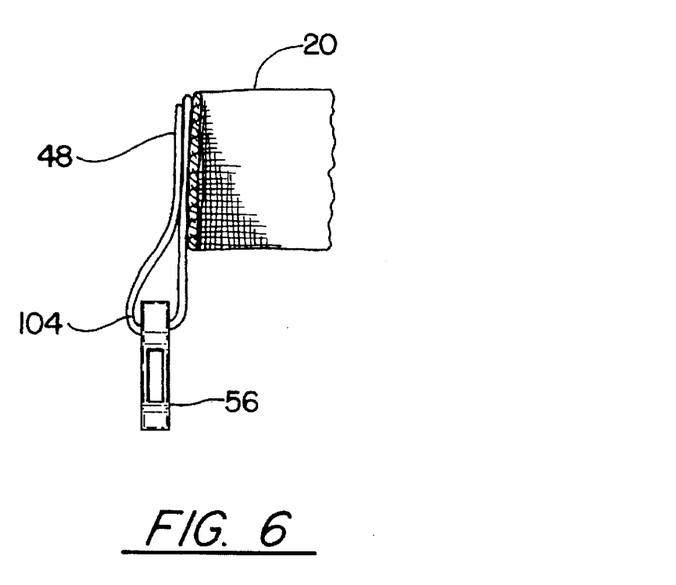
FIG. 6 is a partial cross sectional view taken from line 6—6 of FIG. 3, showing a right thigh strap connecting to a hip or pelvic region strap.
Figure 7:
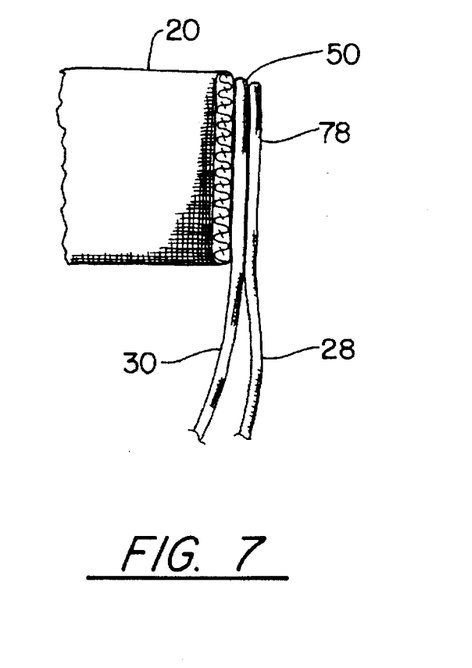
FIG. 7 is a partial cross sectional view taken from line 7—7 of FIG. 3, showing the connection of the right thigh strap and a left thigh strap to the hip strap.

As shown in FIG. 3, the right thigh strap 28 has a first end 48 and a second end 50. The first end 48 is secured to the hip strap 20 at the anterior side 15, the second end 50 is secured to the hip strap 20 at the posterior side at the center point 52. The right thigh strap 28 is secured to the hip strap 20 using nylon stitching. Adjacent to the right thigh strap first end 48 is a length adjustable slide fastener 54. The fastener 54 has a first female portion 56 and a second male portion 58. The male portion 58 has a length adjustment portion 60. The right thigh strap 28 is adapted to wrap around the passenger's right inner thigh and then be fastened together using fastener 54. The length of the right thigh strap 28 then may be adjusted by using length adjustment portion 60, wherein a right thigh strap extension 61 may pulled to shorten the strap 28 or may be fed back through the length adjuster 60 to lengthen the strap 28. As shown in FIG. 6, the right crotch strap 28 is attached together at the first end 48 to create a crotch strap loop 104. The female fastener portion 56 is secured by the loop 104. The left crotch strap 30 has a similar arrangement.

The left thigh strap 30 has a first end 76 and a second end 78. The first end 76 is secured to the hip strap 20 at the anterior side, the second end 78 is secured to the hip strap 20 at the posterior side at the center point 52. The right and left thigh straps 28 and 30 overlay each other at the hip strap posterior side center point 52 and are secured to the hip strap 20 by nylon stitching. Adjacent to the left thigh strap first end 76 is a length adjustable slide fastener 80, which is similar to the fastener 54. The left thigh strap 30 is adapted to wrap around the passenger's left inner thigh and then be fastened together using fastener 80. The length of the left thigh strap 30 then may be adjusted by using the length adjustment feature of the fastener 80.

Figure 8:
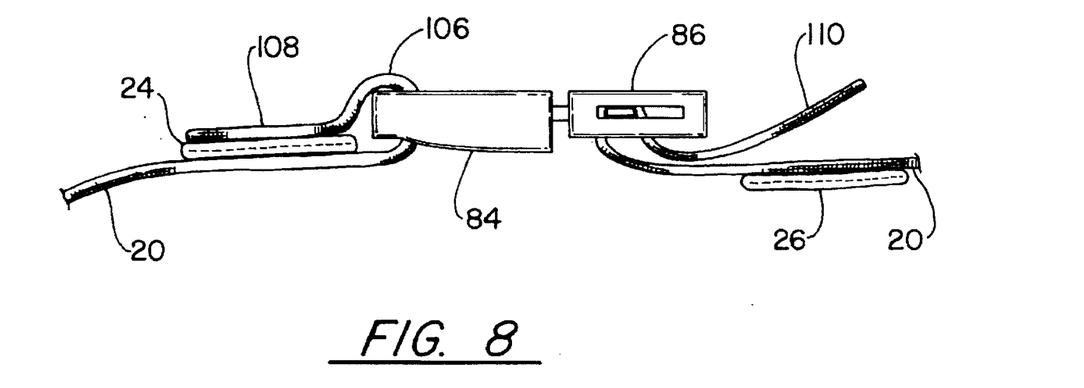
FIG. 8 is a view taken from taken from line 8—8 of FIG. 3, showing a hip strap length adjustable slide fastener and the adjacent hip strap.

The hip strap 20 has a length adjustable fastener 82 located approximately at the center of the anterior side 15 of the harness 10. The fastener 82 has a female portion 84, a cooperating male portion 86, and a release mechanism 85. The male portion 86 has a length adjustable feature, as shown in FIG. 8, wherein the hip strap 20 may be lengthened or shortened by pulling or pushing a hip strap extension 110 through the fastener male portion 86. The hip strap 20 has a folded over portion 108 creating a hip strap loop 106. The fastener female portion 84 is captured by the hip strap loop 106. The chest strap 22 and the and the leg strap 32 have similar arrangements.

The chest strap 22 also has a length adjustable fastener 88 located approximately at the center of the anterior side 15 of the harness 10. The fastener 88 has a female portion 90, a cooperating male portion 92, and a release mechanism 91. The male portion 92 has a length adjustable feature identical to fastener 82.

The leg strap 32 also has a length adjustable fastener 94 located approximately at the center of the anterior side 15 of the harness 10. The fastener 94 has a female portion 96, a cooperating male portion 98, and a release mechanism 97. The male portion 98 has a length adjustable feature identical to fasteners 82 and 88.

The torso straps 20, 22, 24, 26, and the leg strap 32 are made from a commercially available nylon webbing, similar to the material used for automobile seat belts. The thigh straps 28 and 30 are made from a commercially available nylon webbing that is smaller in width than the material used for the other straps. However, the wider nylon webbing used in the torso straps could also be used for the thigh straps 28 and 30.

The fasteners 82, 88, and 94 are similar to commercially available seat belt buckles used for automobiles; however, any length adjustable fastener would be suitable. For example, as explained as a separate embodiment below, hook and loop fasteners with overlapping fastening areas would provide an alternative length adjustable fastening means.

The harness torso portion 11 is fastened around the passenger and fastened together. The harness torso portion 11 is then adjusted to fit snugly on the passenger by tightening the straps with the adjusters. The passenger is then placed on the seat in the supine position. The harness bottom portion 13 is then placed around the passenger's legs and the appliance. The existing seat belts are then fed through the harness torso straps 20 and 22. The seat belt 18a is fed through the chest strap 22, then the seat belt 18a is fastened together and the length is adjusted so that the slack is removed from the seat belt. Seat belt 18b then is fed through the hip strap 20 and the leg strap 32, then the seat belt 18b is fastened together and the length is adjusted so that the slack is removed from seat belt 18b.

After placement of the harness 10 on the passenger and the fastening of the seat belts 18 through the harness, the passenger is secured to the seat 14 in a safe and comfortable supine position so that the passenger may be transported in a vehicle.

Figure 9:
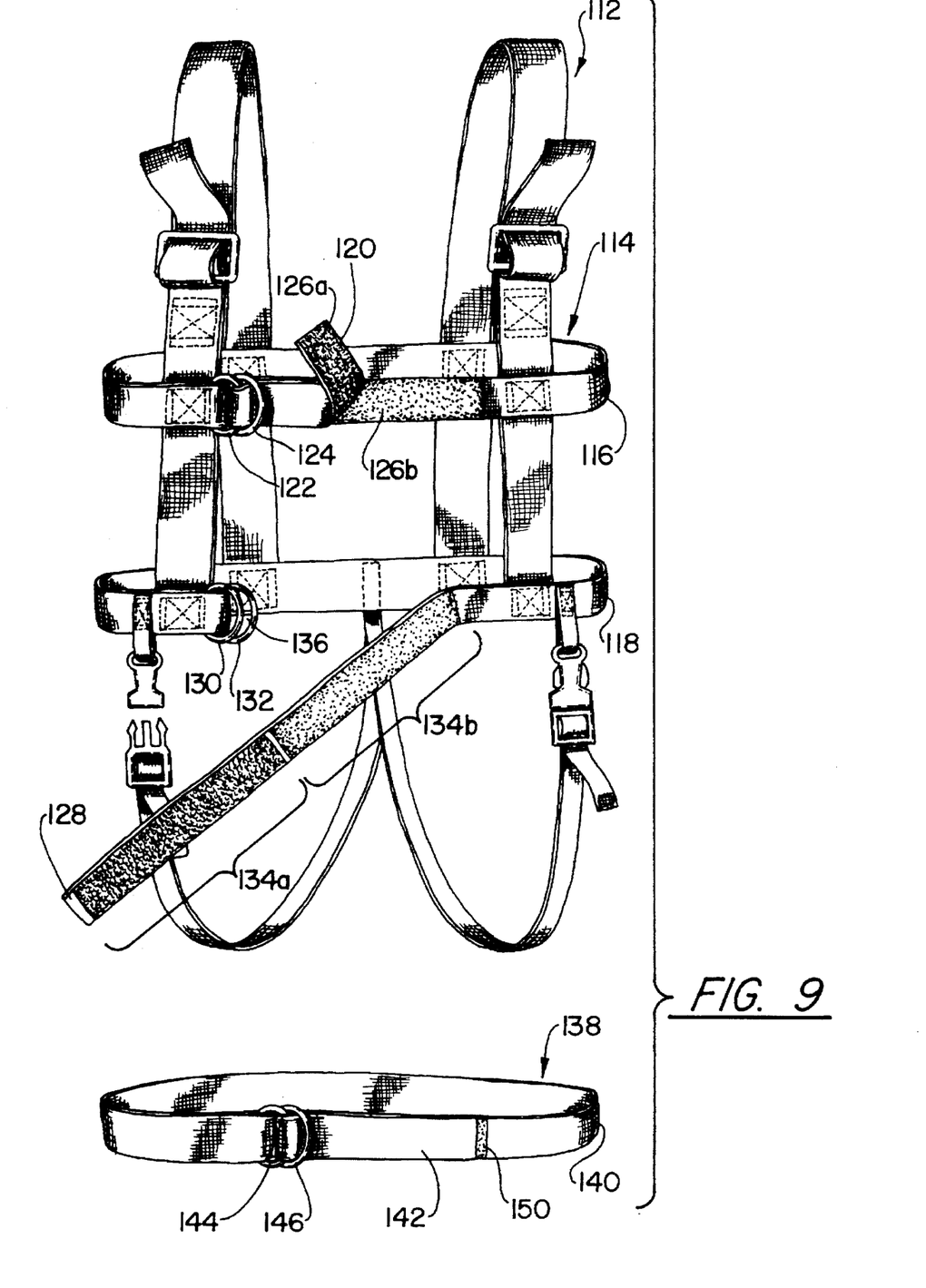
FIG. 9 is a front perspective view of a separate embodiment restraint harness of the present invention.

A separate embodiment of the present invention is shown in FIG. 9, wherein the restraint harness of the separate embodiment is similar to the above described restraint harness except that the adjustable fastening means for the chest strap, the hip strap, and the leg strap comprise hook and loop fasteners.

As shown in FIG. 9, a separate embodiment of a restraint harness 112 of the present invention is shown with the similar features as the restraint harness shown in FIG. 3 and described above, except that the harness 112 has a torso portion 114 and a lower limb portion 138 with each utilizing hook and loop fasteners as the lateral strap adjustable fastening means. The torso portion 114 has a chest strap 116 and a hip strap 118. The chest strap 116 has a chest strap extension 120 that cooperates with a first D-ring 122 and a second D-ring 124. The chest strap extension 120 is placed through the D-rings 122 and 124 and then placed over D-ring 122 and back through D-ring 124. The D-rings 122 and 124 act as a slide for the chest strap extension 120. Complimentary hook and loop fasteners 126 sewn to the chest strap extension 120 cooperate so that as the chest strap extension 120 is placed through the D-rings 122 and 124 and folded over on itself, the hook and loop fasteners 126 fasten the chest strap together. The length of the chest strap 116 may be adjusted depending upon the amount of the chest strap extension 120 that is placed through the D-rings 122 and 124.

The hip strap 118 has a fastening means similar to the chest strap 116. As shown in FIG. 9, the hip strap has a hip strap extension 128, which has hook and loop fasteners 134 sewn to the outside surface of the hip strap extension 128. The hook and loop fasteners 134 have two sections, 134a juxtaposed to a complementary section 134b.

The hip strap 118 has a first D-ring 130 and a juxtaposed second D-ring 132. Similar to the chest strap D-rings, the hip strap D-rings 130 and 132 have a D-ring opening 136 adapted to allow the hip strap extension 128 to be folded between the D-rings 130 and 132 through the D-ring opening 136, so that as the extension is folded over onto itself, the hook and loop fasteners 134 fasten to each other, fastening the hip strap together.

The lower limb portion 138 comprises a similar hook and loop fastening means as the chest and hip straps. The lower limb portion 138 has a leg strap 140 with a leg strap extension 142. The leg strap 140 has a first D-ring 144 and a second D-ring 146. The leg strap extension 142 is folded through the D-rings 144 and 146 and then folded over onto itself. Hook and loop fasteners 150 fasten the leg strap 140 together.

In the separate embodiment of FIG. 9, the harness torso portion 114 is fastened around the passenger and fastened together, using the hook and loop fasteners to adjust the amount of tightness laterally around the torso. The harness torso portion 114 is then adjusted to fit snugly on the passenger by tightening the shoulder straps with the adjusters. The passenger is then placed on the seat in the supine position. The harness lower limb portion 138 is then placed around the passenger's legs and the appliance. The existing seat belts are then fed through the harness torso straps. The seat belt is fed through the chest strap 116, then the seat belt is fastened together and the length is adjusted so that the slack is removed from the seat belt. The adjacent seat belt then is fed through the hip strap and then the leg strap 140, then the seat belt is fastened together and the length is adjusted so that the slack is removed from seat belt.

After placement of the harness on the passenger and the fastening of the seat belts through the harness, the passenger is now secured to the seat in a safe and comfortable supine position so that the passenger may be transported in a vehicle.

Although this invention has been shown and described with respect to a detailed embodiment, those skilled in the art will understand that various changes in form and detail may be made without departing from the spirit and scope of the claimed invention.

I claim:

1. A restraint harness for securing a passenger in a supine position to a vehicle seat having at least one seat belt, said seat belt fastening to said restraint harness, and said restraint harness comprising:

a torso portion and a lower limb portion;

said torso portion comprising a plurality of straps to encompass the passenger's torso;

said lower limb portion comprising at least one leg strap to encompass the passenger's lower limbs; and right and left thigh straps extending from the torso portion and adapted to be placed around the respective thighs of the passenger, each thigh strap including a length adjustable slide fastener.

2. The restraint harness of claim 1, wherein said lower limb strap further comprises a length adjustable fastening means; said leg strap being adapted to encompass the passenger's lower limbs and at least one appliance for a lower limb.

3. The restraint harness of claim 1, wherein said torso straps each further comprise a length adjustable fastening means.

4. The restraint harness of claim 1, wherein said torso straps further comprise:

an anterior side and a posterior side;

a hip strap adapted to fit laterally around the passenger's hip area;

a chest strap adapted to fit laterally around the passenger's chest area, said chest strap being generally parallel to said hip strap;

a right shoulder strap and a left shoulder strap, said shoulder straps extending from each respective shoulder and extending anteriorly and posteriorly along the passenger's torso to intersect with said chest strap and said hip strap at said anterior side and said posterior side, said shoulder straps being fastened to said chest straps and said hip straps.

5. The restraint harness of claim 4, wherein said vehicle seat has a first seat belt and a second seat belt, the seat belts being juxtaposed to each other, said chest strap being adapted to accept said first seat belt; said hip strap and said leg strap being adapted to accept said second seat belt.

6. The restraint harness of claim 4, wherein each said shoulder strap further comprises:

an anterior portion and a posterior portion;

said anterior and posterior portions cooperating with each other by a length adjustable slide fastener so that each said shoulder strap is independently length adjustable.

7. The restraint harness of claim 4, wherein said thigh straps extend from a center point at the posterior side of the hip strap to the anterior side of the hip strap.

8. The restraint harness of claim 4, wherein said chest strap, said hip strap, and said leg strap each further comprise a length adjustable fastening means.

9. The restraint harness of claim 8, wherein each said chest strap, hip strap, and leg strap length adjustable fastening means further comprise a conventional seat belt buckle with a male portion, a mating female portion, a release mechanism, and a length adjustable slide mechanism.

10. The restraint harness of claim 8, wherein said chest strap, said hip strap, and said leg strap length adjustable fastening means each further comprises:

a strap extension with complementary hook and loop fasteners;

at least one ring to comprise a slide mechanism, so that the strap extension may be fed through the ring and folded over upon itself to be fastened releasably by the hook and loop fasteners.

11. The restraint harness of claim 8, wherein said straps are made of a nylon webbing material.

12. A restraint harness for securing a passenger in a supine position to a vehicle seat having a seat belt, comprising:

a torso portion having a pair of shoulder straps and a pair of lateral straps;

said lateral straps comprising a chest strap and a hip strap, said lateral straps being adapted to fit laterally across the passenger's chest area and hip area, said lateral straps being generally parallel with each other;

said shoulder straps being adapted to fit over the passenger's shoulders, said shoulder straps extending anteriorly and posteriorly to said hip strap so that said shoulder straps intersect with said chest strap and said hip strap, said shoulder straps being generally perpendicular to said lateral straps, said shoulder straps and said lateral straps being fastened together;

said lateral straps having fastening means so that the straps may be fastened and unfastened around the torso of the passenger;

a lower limb portion comprising a leg strap and adapted to be fitted laterally around the passenger's lower limbs;

said lower limb portion having fastening means so that said leg strap may be fastened and unfastened around the lower limbs of the passenger;

right and left thigh straps extending from the torso portion and adapted to be placed around the respective thighs of the passenger, each thigh strap including a length adjustable slide fastener.

13. The restraint harness of claim 12, including a posterior side and an anterior side;

said thigh straps extend from a center point at the posterior side of the hip strap to the anterior side of the hip strap.

14. The restraint harness of claim 12, wherein the lateral straps fastening means and the leg strap fastening means are length adjustable;

said leg strap being adapted to encompass the passenger's lower limbs and at least one appliance for a lower limb.

15. The restraint harness of claim 14, wherein each said chest strap, hip strap, and leg strap length adjustable fastening means further comprise a conventional seat belt buckle with a male portion, a mating female portion, a release mechanism, and a length adjustable slide mechanism.

16. The restraint harness of claim 14, wherein said chest strap, said hip strap, and said leg strap length adjustable fastening means each further comprises:

a strap extension with complementary hook and loop fasteners;

at least one ring to comprise a slide mechanism, so that the strap extension may be fed through the ring and folded over upon itself to be fastened releasably by the hook and loop fasteners.

17. The restraint harness of claim 14, wherein said straps are made of a nylon webbing material.

* * * * *